United States Patent [19]

Marchal et al.

[11] Patent Number: 6,013,241
[45] Date of Patent: Jan. 11, 2000

[54] USE OF PORPHYRIN-COMPLEX OR EXPANDED PORPHYRIN-COMPLEX COMPOUNDS AS AN INFARCTION LOCALIZATION DIAGNOSTICUM

[75] Inventors: Guy Jacques Felix Marchal, Oud-Heverlee; Yicheng Ni, Leuven, both of Belgium

[73] Assignee: Schering Aktiengesellschaft, Netherlands

[21] Appl. No.: 08/818,411

[22] Filed: Mar. 17, 1997

Related U.S. Application Data

[63] Continuation of application No. 08/375,919, Jan. 23, 1995, abandoned.

[51] Int. Cl.[7] .......................... A61K 51/04; A61K 49/00; A61B 5/055
[52] U.S. Cl. .................. 424/1.65; 424/9.362; 424/9.61
[58] Field of Search .................. 424/1.65, 9.362, 424/9.61, 9.36, 9.361; 534/10, 11, 12, 13, 14, 15, 16; 540/145

[56] References Cited

U.S. PATENT DOCUMENTS 5,284,647  2/1994  Niedballa et al. .................. 424/81

FOREIGN PATENT DOCUMENTS 937194   6/1994  South Africa .
9206097  4/1992  WIPO .......................... C07D 487/22

OTHER PUBLICATIONS

The New International Webster's Comprehensive Dictionary of the English Language, 1996 Edition, pp. 1204–1205.

Ince et al., "Heterogeneity of the hypoxic state in rat heart is determined at capillary level." American Journal of Physiology: Heart and Circulatory Physiology, vol. 33, No. 2, pp. 295–301 (1993).

Bockhorst et al., "Localization of Experimental Brain Tumors in MRI by Gadolinium Porphyrin," Acta Neurochir, 60: 347–349 (1994).

Ross et al., "Myoglobin as an Oxygen Indicator for Measuring the Oxygen Binding Characteristics of a Modified Myoglobin Derivative Containing Covalently Bound Mesoheme," Pennsylvania State University (1977).

*Primary Examiner*—Jose' G. Dees
*Assistant Examiner*—Michael G. Hartley
*Attorney, Agent, or Firm*—Webb Ziesenheim Logsdon Orkin & Hanson, P.C.

[57] ABSTRACT

The invention relates to the use of porphyrin-complex or expanded porphyrin-complex compounds for the manufacture of a diagnosticum for the localization of an infarction and of a necrosis, wherein the infarction or necrosis may comprise an infarction of heart, kidney, intestine, lung, and/or brain, and wherein the porphyrin-complex compound may be Gd-MP and/or Mn-TPP.

5 Claims, 4 Drawing Sheets

USE OF PORPHYRIN-COMPLEX OR EXPANDED PORPHYRIN-COMPLEX COMPOUNDS AS AN INFARCTION LOCALIZATION DIAGNOSTICUM

This application is a continuation of application Ser. No. 08/375,919 filed on Jan. 23, 1995, now abandoned.

BACKGROUND OF THE INVENTION

1. Field of the Invention

The present invention relates to the use of porphyrin-complex and expanded porphyrin-complex compounds for use as a diagnosticum, in particular for use as a diagnosticum for the detection, localization, and monitoring of an infarction, and of a necrosis.

2. Description of the Prior Art

Suitable porphyrin-complex compounds are subject of DE-A-4,232,925, DE-A-4,305,523, EP-A-336,879, and EP-A-355,041. The subject matter of these applications are included by cross reference.

These porphyrin-complex compounds are used as a pharmaceutical preparation for the diagnosis and therapy of tumours.

Other suitable porphyrin-complex compounds are expanded prophyrin-complex compounds (17).

The present invention is based on the insight that these porphyrin-complex compounds can be used for the detection, localization, and monitoring of an infarction, and of a necrosis.

Hereafter the use as an infarction localization diagnosticum is primarily exemplified for a myocardial infarction and for a renal infarction, but it will be obvious for a skilled person that due to similar pathophysiological situations the same experimental findings apply to other infarction such as those of the intestines, lung, brain and the like.

Myocardial infarction is not a stable pathophysiological situation, but instead progresses to its definite form over several weeks to months. This process can be subdivided, although overlapping, in at least three periods. The first 24 hours after the start of ischemia (acute evolving myocardial infarction) damage progresses as a wavefront phenomenon from the subendocardium to include the myocardium transmurally. During the second phase (established myocardial infarction) this area stabilizes and fibrosis is formed as a healing process. The third phase (healed infarction) starts after all the damaged tissue is replaced by a fibrotic scar. During this phase, considerable remodelling takes place. So far no accurate and reliable technique exists that can determine the evolution phase of the myocardial infarction antemortem.

The most important long-term prognostic factor after a myocardial infarction is the amount of myocardial tissue lost during this process. So far, no accurate and reliable technique exists to demonstrate the end-point, the amount of irreversibly damaged tissue antemortem.

In the three phases described above, it is of extreme importance to have an accurate status about the amount and localization of the affected myocardial tissue. During an evolving myocardial infarction, it is important to assess the amount of tissue at risk, the amount already lost, and from these parameters the amount of tissue that can be salvaged by reperfusion by thrombolysis or emergency surgical revascularisation, according to the hemodynamic status of the patient. In a patient with unstable angina, it is often impossible to discriminate between reversibly injured (akinetic, stunned) myocardium and irreversibly damaged tissue. This would nevertheless have a profound impact on the therapeutic strategy. In the case of complications in the phase of established infarction: requiring surgical intervention, it is known that mortality is highest when dead tissue is revascularized, causing hemorrhagic infarctions. An operative strategy of repair of the ventricular septum defect or mitral insufficiency with selective revascularisation of non-necrotic tissue could save lives.

Up to now, a satisfactory in vivo method for localizing and defining an infarction and the size of an infarction has not yet been available, which impedes the progress of both the basic research and clinical practice (1). For instance, current imaging techniques such as echocardiography (2), nuclear scintigraphy with perfusion and infarct avid tracers (3–5) and magnetic resonance imaging (MRI) without and with different contrast media (6–9) are still far from optimal in terms of sensitivity, specificity, spatial resolution, contrast and reliability (3).

Similar contemplations apply for infarctions of the kidney intestines, lung and brain.

Necrosis is a status of local tissue death, and results from the effects of diseases resulting in an adverse and detrimental effect on body tissue. Necrosis may be caused by radiation, injury, chemicals, local oxygen deficiency, infections, cancer, and the like. Monitoring, localization and detection of necrosis allows the follow up and effectiveness determination of all kinds of diagnostic and therapeutic therapies and treatments.

SUMMARY OF THE INVENTION

The present invention relates to the use of these porphyrin-complex compounds or metalloporphyrins, for the localization, visualization of an infarction and of a necrosis. This invention is based on experimental results with myocardial and renal infarctions, and with hepatic, renal and muscle necrosis demonstrating an extraordinary effect with one-to-one correlation between magnetic resonance images (MRI) and histochemical preparations. This preclinical result opens new horizons for especially the cardiac and necrotic imaging.

DESCRIPTION OF THE PREFERRED EMBODIMENTS

Figures 1A, 1B:
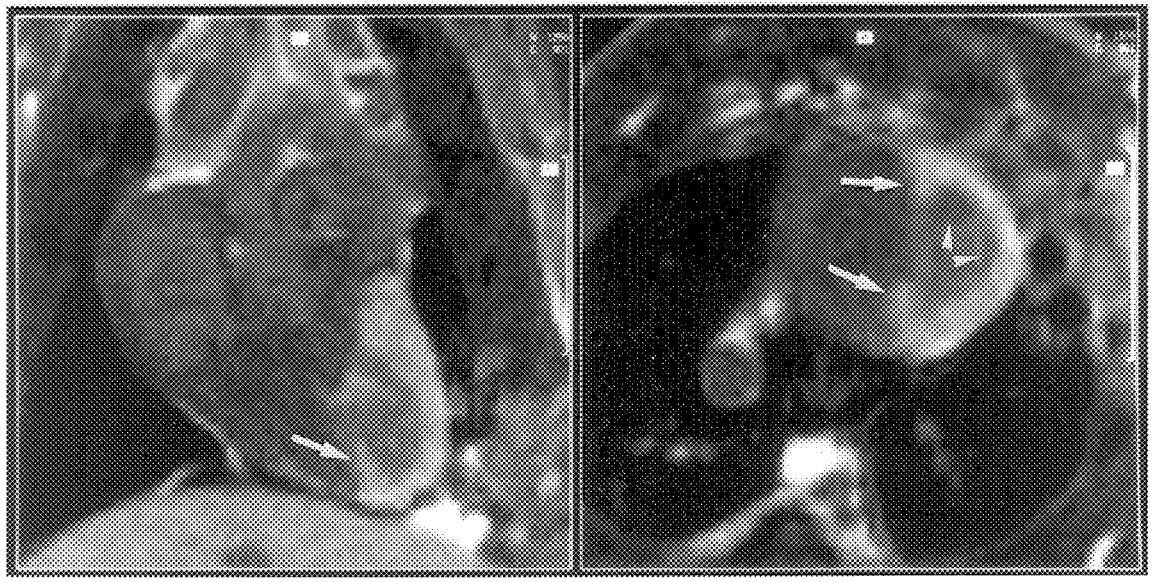
FIGS. 1A–C are macroscopic photographs of a rodent heart with myocardial infarction.

The porphyrin-complex compounds comprise a ligand having the general formula I

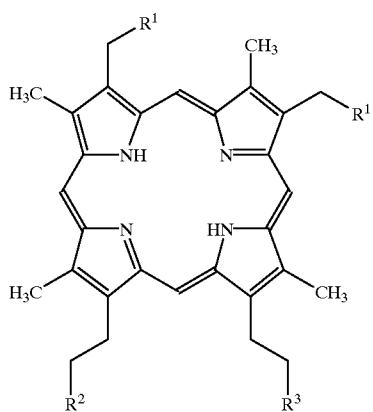

(I)

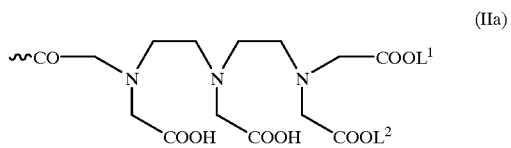

(IIa)

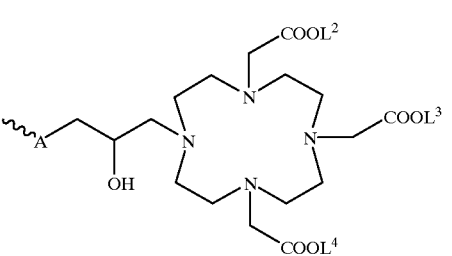

(IIb)

and at least one metal ion suitable for ex corporal determination. Suitable metal ions have an atomic number of 21-32, 37-39, 42-51 and 57-83.

In this general formula:

$R^1$ represents a hydrogen atom, a straight or branched $C_1$–$C_6$ alkyl group, a $C_7$–$C_{12}$ aralkyl group or a OR' group wherein R' is a hydrogen atom or a $C_1$–$C_3$ alkyl group, $R^2$ represents a group CO-Z or a group $(NH)_o$—$(A)_q$—NH—D, wherein Z is a group OL with L is an inorganic or organic cation or a $C_1$–$C_4$ alkyl group, A is a phenylenoxy group, a $C_2$–$C_{12}$ alkylene group possibly interrupted by one or more oxygen atoms, or a $C_7$–$C_{12}$ aralkylene group, o and q independently represent an integer 0 or 1, and D represents an hydrogen atom or a group CO—A (COOL)$_o$—(H)$_m$ with m equals 0 or 1 under the provisio that the sum of m and o equals 1;

$R^3$ represents a group (C=M) $(NR^4)_o$—$(A)_q$—$(NR^5)$—K, CO—Z or $(NH)_o$—$(A)_q$—NH—D wherein Z is OL; wherein L is selected from the group consisting of an inorganic cation, an organic cation, or a $C_1$–$C_4$ alkyl group; wherein A is selected from the group consisting of a phenylenoxy group, a $C_2$–$C_{12}$ alkylene group having zero or more oxygen atoms, or a $C_7$–$C_{12}$ aralkylene group; wherein o and q independently equal 0 or 1; wherein D is selected from the group consisting of hydrogen and CO—A (COOL) $_o$—(H)$_m$ where m equals 0 or 1 under the proviso that the sum of m and o equals 1; and wherein M represents an oxygen atom or two hydrogen atoms;

$R^4$ represents a group $(A)_q$—H; and

K represents a complex former having the general formula IIa or IIb, and $R^5$ when K is formula IIa has the same meaning as $R^4$ and when K has the formula IIb has the same meaning as D, under the proviso that a direct oxygen-nitrogen bond is not allowed, wherein $L^1$ has the meaning of a $C_1$–$C_6$ alkyl group or an inorganic or organic cation and wherein $L^2$, $L^3$ and $L^4$ independently have the same meaning as $L^1$ or are an hydrogen atom, under the proviso that the complex former comprises at least two free carbon acid groups, and optionally for charge mutualization of the metalloporphyrin other anions, and pharmaceutically acceptable addition salts and carriers and diluants.

For MR localization the porphyrin-corplex compounds comprises at least one paramagnetic metal ion, preferably di- or trivalent ions of the metal elements having the atomic number 21-29, 42, 44 and 57-70. Suitable metal ions are for instance chromium (III), manganese (II), manganese (III), iron (III), cobalt (II), cobalt (III), nickel (II), copper (II), praseodymium (II), neodymium (III), samarium (III) and ytterbium (III). Prefered are gadolinium (III), terbium (III), dysprosium (III), holmium (II), erbium (III) and iron (III).

For radioscintigraphic determination radioisotopes of the elements having the atomic number 27, 29-32, 37-39, 42-51, 62, 64, 70, 75, 77, 82 or 83 are preferred.

It is noted that when the complex compounds comprises various metal ions these metal ions may originate from the group for MR visualization and radioscintigraphic visualization.

Futhermore the metal ion may be complexed in the porphyrin skeleton, in the so called expanded porphyrin skeleton, and/or in the complex former.

Examples of the porphyrin-complex compounds are the disodium salt of the digadolinium complex of N,N'-Bis[9-carboxylato- 2,5,8-tris(carboxlatomethyl)-2,5,8-triazanonyl-carbamoyll-mesoporphyrin-IX-13,17-diamides (Gd-MP). The disodium salt of the digadolinium complex of manganese (III)- N,N'-Bis[11-carboxylato-2-oxo-4,7-bis (carboxylatomethyl)-10-(ethoxycarbonylmethyl)-1,4,7,10-tetraazaundecyl]-3,8-bis(1-propyl)-porphyrin-IX-13,17-diamides-acetates, and the digadolinium complex of manganese (III)- N,N'-Bis[11-carboxylato-2-oxo-4,7-bis (carboxylatomethyl)-10- (ethoxycarbonylmethyl)-1,4,7,10-tetraazaundecyl]-3,8-bis(1-propyl)-porphyrin-TX-13,17-diamides-acetates (Mn-TPP).

The diagnosticum has the form of a pharmaceutical formulation suitable for intra-veneous or intra-arterial injection in the form of a solution or suspension. The diagnosticum may comprise suitable additives, such as a buffer (tromethamine), complex formers such as diethylenetriaminpenta-acetic acid, electrolyte such as sodium chloride, antioxydantia such as ascorbiic acid.

Furthermore additives, tencides and the like may be added.

Gd-MP

Bis-Gd-DTPA-{Mesoporphyrin-IX-13, 17-bis[2-oxo-4, 7, 10, 10-tetra-(carboxylatomethyl)-1, 4, 7, 10-tetraazadecyl]-13, 17-diamide}, bis sodium salt

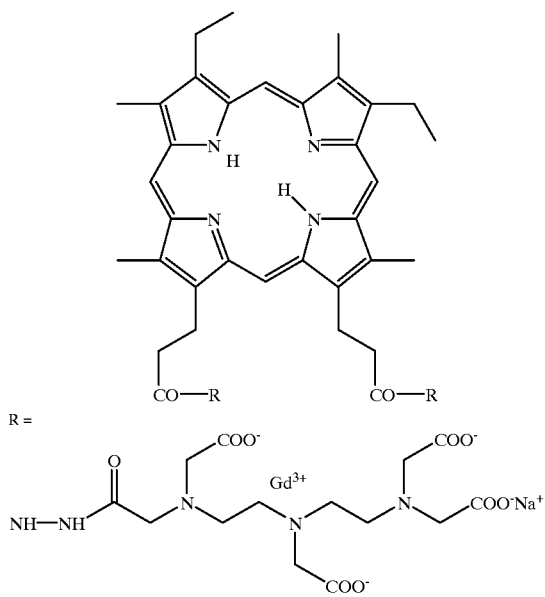

Mn-TPP
Manganese-(III)-{Tetrakis-[3]-(carboxylatmehoxyphenyl)-porphyrin}acetate, tetra sodium salt

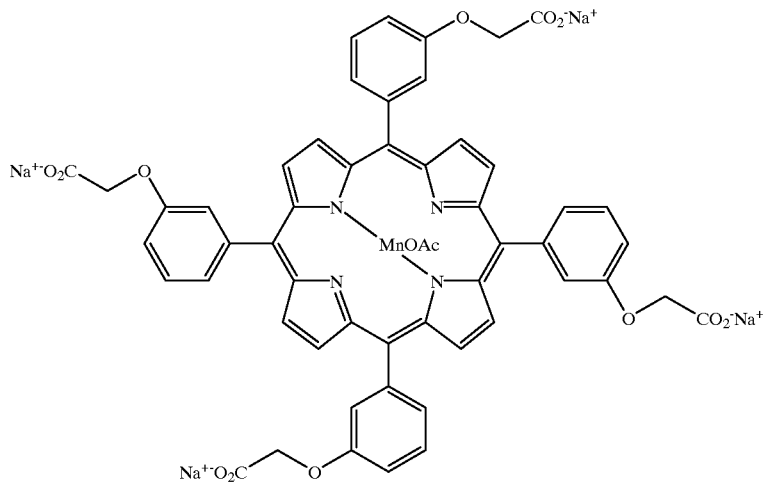

The diagnosticum may comprise the porphyrin or expanded porphyrin complex compound in an amount of 0.0001–10.0 mmol/kg body weight. Preferred is an amount of 0.005–2 mmol/kg body weight, more preferred 0.01–1.0 mmol/kg body weight. The actual dose is also dependent on the infarction to be localized, on the patient and on the localization technique to be used.

Hereafter the use of a diagnosticum comprising these specific metalloporphyrins, for the localization of an infarction and of necrosis, according to the invention will be shown for the visualization of an acute myocardial infarction and renal infarction, and of necrosis. The result obtained so far did not encounter either false positive nor false negative findings. Strikes is the almost perfect matching of the ex corporal localization and the histochemical confirmation.

In the experiments two paramagnetic metalloporphyrins have been used which were originally developed as potential tumour specific MRI contrast agents (10–14). Gadolinium mesoporphyrin (Gd-MP) and manganese tetraphenylporphyrin (Mn-TPP) have been used.

EXAMPLE 1

The model of myocardial infarction was produced in rats by ligation of the left coronary artery according to an established technique (15). Two groups of rats (12 in each) with myocardial infarction aging 2 to 24 hours received intravenously either Gd-MP (IDF GmbH, Berlin) or Mn-TPP (IDF GmbH, Berlin) at doses of 0.1, 0.05 and 0.01 mmol/kg (4 rats each). After an interval of 3 to 24 hours postinjection, axial and coronal T1 weighted spin echo MR images were obtained immediately before and after sacrificing the animals. The excised heart was incubated with triphenyl tetrazolium chloride (TTC), which is a reliable histochemical staining to distinguish the infarcted from the non-infarcted myocardium (16). In addition, two groups of rats (6 in each) were used as controls and underwent the same imaging and histochemical procedures, i.e. one group with infarction but without contrast agent injection, the other group with injection (3 with Gd-MP, 3 with Mn-TPP) but without infarction. The difference between the infarcted and non-infarcted myocardium seen on MR images was quantified by measuring the signal intensities (SI) with a monitor defined region of interest and expressed as contrast ratio (CR):CR=SI infarct/SI noninfarct (mean±SD). The metal content of the tissue was measured by ICP-AES. Finally the MR images were carefully compared with the corresponding macro- and microscopic tissue preparations and correlated with the results of local metal content measurement.

Figure 1C:
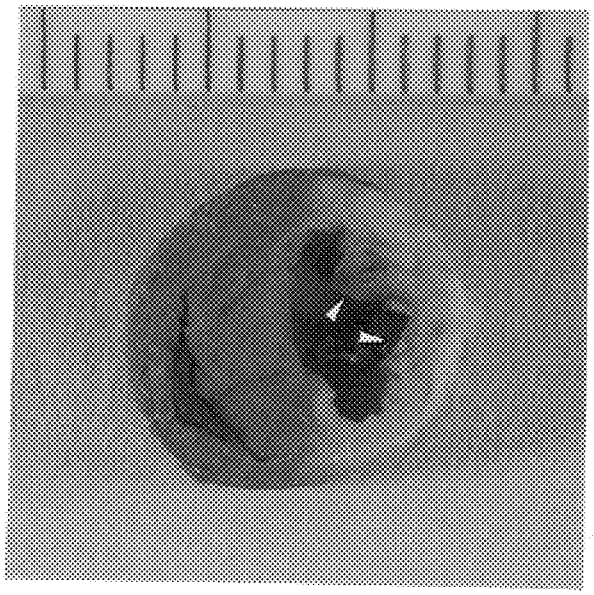

The infarct of the 6 control rats could not be discerned by MRI without contrast media. However, 3 to 24 hours after injection of either Gd-MP or Mn-TPP, all 24 rats with myocardial infarction exhibited on MR images a clear delineation of the infarcted areas of the heart, which precisely matched the areas of negative staining on the histochemical samples (FIG. 1). The CRs between the infarcted and noninfarcted regions were 3.40±0.26 at 3 hours and 1.92 ±0.17 at 24 hours after contrast agent injection. Even the small dose of 0.01 mmol/kg worked well (CR=1.84±0.13 at 10 hours postinjection). Neither false positive findings (i.e. contrast enhancement in noninfarcted area) nor false negative findings (i.e. infarcted myocardium not enhanced with the agents) were obtained. The Gd content was as much as 9 fold higher in the infarcted myocardium (Table 1), suggesting that the MPI signal enhancement is mainly due to a preferential accumulation of metalloporphyrins in infarcted tissue.

EXAMPLE 2

Using the same model of myocardial infarction, in two rats minor necrotic lesions were found at the ligation sides.

Figures 2A, 2B:
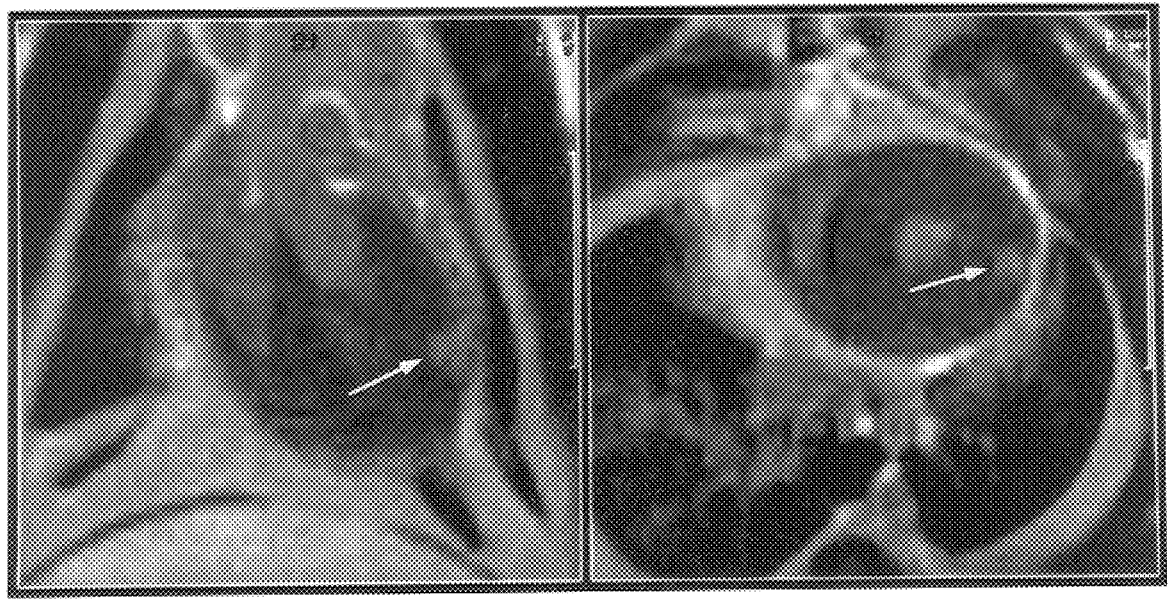
FIGS. 2A–C are macroscopic photographs of a rodent heart with local injury caused by ligation.
Figure 2C:
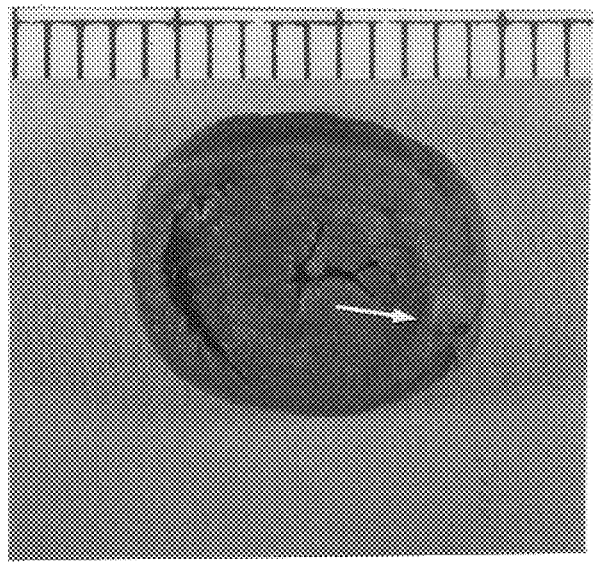

The MRI was performed 10 hours after Mn-TPP (0.05 mmol/kg body weight) intervenous injection. The technique is so sensitive that even lesions between 1 to 2 mm in size were easily detectable (FIG. 2).

EXAMPLE 3

A rat with partial renal infarction of the right kidney was injected with Gd-MP (0.1 mmol/kg body weight by intervenous injection).

Figures 3A, 3B, 3C:
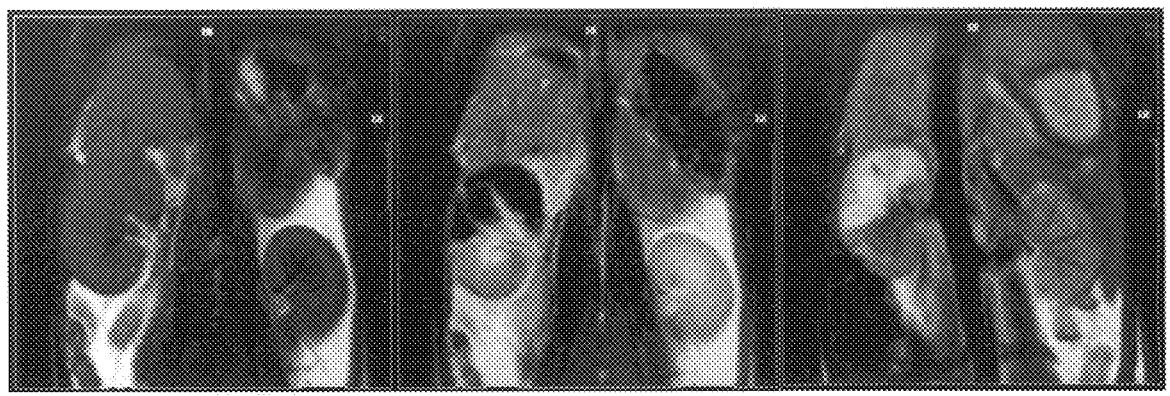
FIGS. 3A–D are MRI and macroscopic photographs of a rat with a partial renal infarction in the right kidney.
Figure 3D:
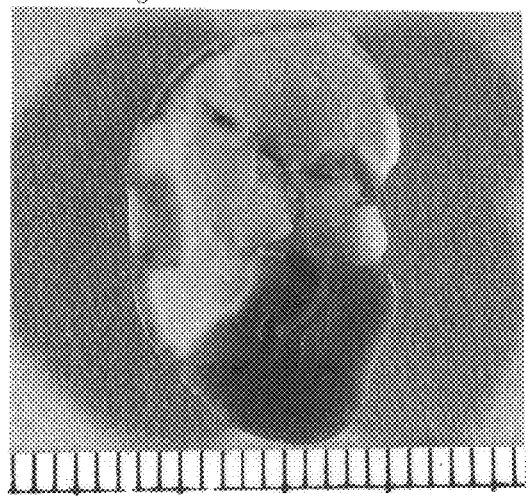

24 Hours after Gd-MP injection, the Gd-content (measured with ICP-AES technique) of the infarcted and non infarcted kidney were similar but the signal intensities were at least two fold higher for the infarcted kidney (Table 2). Presumably the mechanism for metalloporphyrin induced specific enhancement seems not only related to an accumulation of the porphyrin-complex compound in the infarcted tissue. An increased relaxivity of the metalloporphyrins induced by a change in local molecular environment plays also a role in the observed increased signal intensity (FIG. 3).

EXAMPLE 4

In order to evaluate the potential of these agents for the detection and monitoring of other types of necrosis following experiments were performed.

Figures 4A, 4B, 4C:
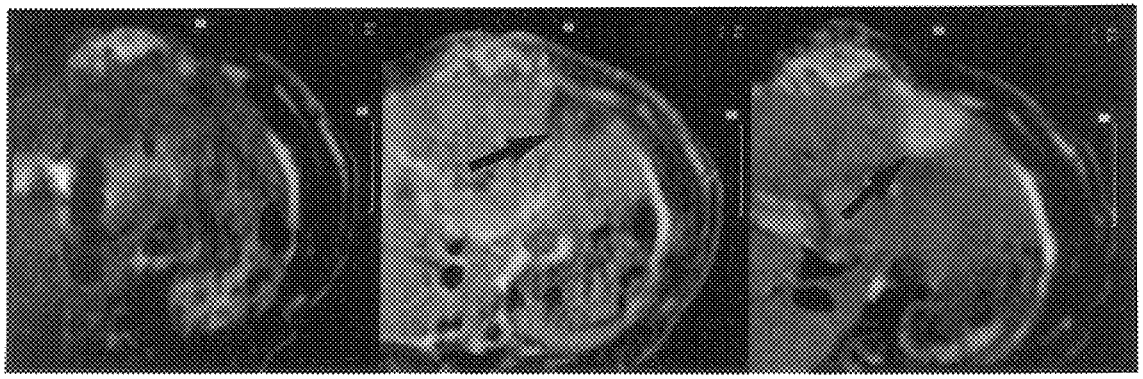
FIGS. 4A–D are axial T1 W SE MR images and macroscopic photographs of a rat liver with alcohol induced coagulation necrosis.

Spontaneous liver necrosis was induced by ligation of the common bile duct in rats. 72 Hours after surgery both types of metalloporphyrins (Gd-MP and Mn-TPP) were intravenously injected at a dose of 0.05 mmol/kg. Already 10 minutes after injection areas of strong enhancement could be observed in the liver. This enhancement lasted for about one week. Macroscopic examination confirmed that the enhancing areas corresponded to cholestatically related liver necrosis. A second experiment consisted in the induction of local necrosis in liver, kidney and muscle in rats by local injection of absolute alcohol. Imaging 8 to 24 hours after alcoholisation of both metalloporphyrins caused a concentric enhancement of the induced lesions. Those remained enhanced for several days. Macroscopy and microscopy after sacrifice confirmed the necrotic nature of the lesions (FIG. 4A, 4B, 4C).

The fact that necrosis of different origin, vascular and biliary infarction and alcoholisation, all show similar degrees of enhancement opens new prospectives for the monitoring of therapies that ultimately cause tissue necrosis, such as radiotherapy, chemotherapy, thermotherapy, laser therapy, ultrasound and radiofrequency ablation, alcoholisation, etc. . . .

TABLE 1

Gd content and MRI signal intensity in rats with myocardial infarction measured 24 hours after Gd-MP (0.05 mmol/kg)

| Myocardium | Gd ($\mu$mol/g) ICP-AES | Signal Intensity (ROI) |
| --- | --- | --- |
| infarcted | 0.065 ± 0.006 | 422 ± 31 |

TABLE 1-continued

Gd content and MRI signal intensity in rats with myocardial infarction measured 24 hours after Gd-MP (0.05 mmol/kg)

| Myocardium | Gd ($\mu$mol/g) ICP-AES | Signal Intensity (ROI) |
| --- | --- | --- |
| non infarcted | 0.007 ± 0.002 | 193 ± 17 |
| ratio* | 9.29 | 2.19 |

Note:
*infarcted/non infarcted

TABLE 2

Gd content and signal intensity in a rat with partial renal infarction measured 24 hours after Gd-MP (0.1 mmol/kg)

| Tissue | Gd ($\mu$mol/g) ICP-AES | Signal intensity (24 h) |
| --- | --- | --- |
| infarcted kidney | 0.75 | 1340 |
| non-infarcted kidney | 0.79 | 638 |

Legends for Figures

FIG. 1 (A–C). MRI and macroscopic photographs of a rodent heart with myocardial infarction. The MRI was performed 24 hours after Gd-MF (0.1 mmol/kg) intravenous injection and immediately after sacrificing the animal.

A, B: Coronal (A) and axial (B) T1 weighted spin echo images (TR/TE=300/15 msec, slice thickness=2 mm, FOV= 100 mm, matrix size=256×256, NEX=6) display a strongly signal enhancment in almost all left ventrical wall including part of the ventricular septum (arrows) but not some papillary myocardial structures (arrowheads). The graduation near the frame on the right side represents 1 cm.

C: Axial section of the heart on a similar plane to the axial MR image (B), incubated with 1% triphenyl tetrazolium chloride (TTC) for 15 minutes and fixed overnight with 10% formalin, shows the left ventrical wall including part of the septum as unstained, (pale) infarcted area. Arrowheads indicate the intact myocardial papillae shown in B.

FIG. 2 (A–C). MRI and macroscopic photographs of a rodent heart with local injury caused by ligation. Such minute necrotic lesions were found at the ligation sites in two rats who failed to form real infarction and were excluded as successful models from the study. The MRI was performed 10 hours after Mn-TPP (0.05 mmol/kg) intravenous injection and immediately after sacrificing the animal.

A, B: On both the coronal (A) and axial (B) MR images (the same parameters as in FIG. 1), an hyperintense lesion (arrow) of approximately 1 mm in size can be clearly seen in the left ventricular wall, despite a partial volume effect (i.e. the diameter of the lesion is smaller an the thickness of the MR slice; otherwise the lesion would appear brighter). The graduation near the frame on the right side represents 1 cm.

C: TTC stained axial section of he heart on a similar plane to the MR image (B) displays the ligature and adjacent minute unstained necrotic lesion (arrow).

FIG. 3 (A–D). MRI and macroscopic photographs of a rat with partial renal infarction in the right kidney A–C: Axial T1 weighted spin eho images (TR/TE=600/15 msec, the rest parameters are the same as in FIG. 1A and B.

A: On precontrast plain scan in the right kidney, infarcted and noninfarcted parts cannot be discerned.

B: Ten minutes after Gd-MP 0.1 mmol/kg) intravenous injection, the noninfarcted parenchyma (lower part) is strongly enhanced in contrast with the unenhanced infarcted parenchyma (upper part), which is gradually filled up with time by the agent (images not shown).

C: Forty-eight hours postcontrast, when the signal intensity of the noninfarcted kidney (lower part) has almost normalized, the infarcted upper part of the kidney is still strikingly enhanced.

D: Macroscopic view of the right kidney on a similar section as in C. Note how well the areas of the infarcted and noninfarcted parenchyma seen on the specimen match with the contrast enhanced MR image (C).

Figure 4D:
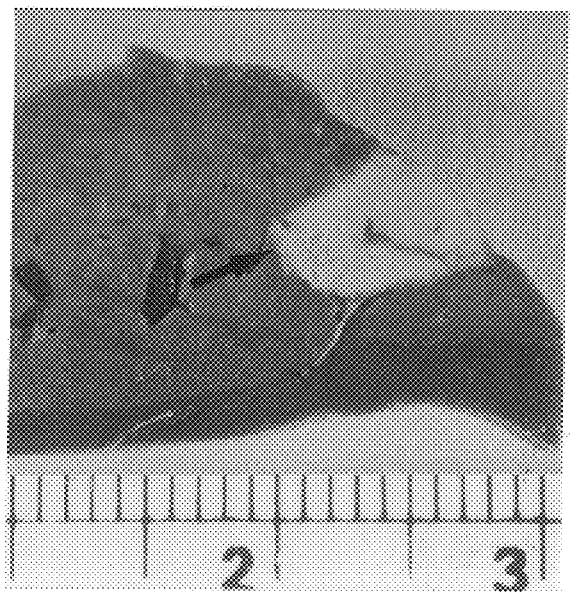

FIG. 4 (A–D). Axial T1 W SE MR images and macroscopic photographs of rat liver with alcohol induced coagulation necrosis.

A: On precontrast image, the 10 hours old necrotic lesion (arrow) is isointense and therefore cannot be detected.

B: Ten minutes after intravenous injection of gadolinium mesoporphyrin (Gd-MP, 0.05 mmol/kg), the lesion (arrow) appears hypointense with some central bright spots (blood vessels). The lesion concentrically enhances with time whereas the liver intensity progressively decreases (images not shown).

C: Twenty-four hours later when the liver intensity has largely decreased, the bright coagulation lesion appears bright (arrow) with some central dark spots. This suggests a specific retention and a strong affinity of the metalloporphyrin for the necrosis.

D: Macroscopic photograph of the liver section in the plane similar to MR images. The alcohol induced coagulation necrosis (arrow) has the same morphology with some intralesional blood vessels, as shown on the contrast enhanced MR images.

References

1. Roberts R, Kleiman N S. Earlier diagnosis and treatment of acute myocardial infarction necessitates the need for a 'new diagnostic mind-set'. Circulation 1994; 89: 872–881.
2. Stamm R, Gibson R, Bishop H, Carabello B, Beller G, Martin R, Echocardiographic detection of infarct-localized asynergy and remote asynergy during acute myocardial infarction: correlation with the extent of angiographic coronary disease. Circulation 1983; 67: 233–234.
3. Wackers F J T, Busemann Sokole E, Samson G et al. Value and limitations of thallium-201 scintigraphy in the acute phase of myocardial infarction N Engl J Med 1976; 295:1–5.
4. Lahiri A, Bhattacharya A, Carrio I. Antimyosin antibody imaging of myocardial necrosis. In; Zaret B L, Beller G A, eds. Nuclear cardiology: state of the art and future directions. Philadelphia: Mosby—Year Book, 1993; 331–338.
5. Zaret B L, Wackers F J. Nuclear cardiology (review). N Engl J Med 1993; 329:775–783.
6. De Roos A., Van Rossum A., Van der Wall E., Postema S., Doornbos J. Matheijssen N. Reperfused and nonreperfused myocardial infarction: diagnostic potential of Gd-DTPA-enhanced MR Imaging. Radiology 1989; 172: 717–720.
7. Saeed M., Wendland M., Takehara Y., Masui T., Higgins C. Reperfusion and irreversible myocardial injury: identification with a nonionic MR imaging contrast medium. Radiology 1992; 182: 675–683.
8. Weissleder R., Lee A., Khaw B., Shen T., Brady T. Antimyosin-labeled monocrystalline iron oxide allows detection of myocardial infarct: MR antibody imaging. Radiology 1992; 182:381–385.
9. Johnston D, Thompson R, Liu P. Magnetic resonance imaging during acute myocardial infarction Am J Cardiol 1986; 58: 214–219.
10. Chen. C, Cohen J., Myers C., Sohn M. Paramagnetic metalloporphyrins as potential contrast agents in NMR imaging. FEBS letters 1984; 168: 70–74.
11. Nelson J., Schmiedl U., Shankland E. Metalloporphyrins as tumor-seeking MRI contrast media and as potential selective treatment sensitizers. Invest Radiol 1990; 25: S71–73.
12. Nelson J., Schmiedl U. Porphyrins as contrast media. Magn Res Med 1991; 22: 366–371.
13. Ogan M., Revel D., Brasch R. Metloporphyrin contrast enhancement of tumors in magnetic resonance imaging. A study of human carcinoma, lymphoma, and fibrosarcoma in mice. Invest Radiol 1987; 22: 822–828.
14. Van Zijl P C M, Place D A, Cohen J S, Faustino P J, Lyon R C, Patronas N J. Metalloporphyrin magnetic resonance contast agents: feasibility of tumor-specific magnetic resonance imaging. Acta Radiol suppl (Stockh)1990; 374: 75–79.
15. Selye H, Bajusz E., Grasso S., Mendell P. Simple technique for the surgical occlusion of coronary vessels in the rat. Angiology 1960; 11: 398–407.
16. Fishbein M., Meerbaum S., Rit J., Lando U., Kanmatsuse K., Merder M, et al. Early phase acute myocardial infarct size quantification: validation of the triphenyl tetrazolium chloride tissue enzyme staining technique. Am Heart J 1981 101: 593–600.
17. Sessler J. L. et al. Expanded porphyrin, synthesis and structure of a new aromatic pentadentate ligand, J.Am-.Chem.Soc. 1988; 110: 5586–5588.

We claim:

1. A method of specifically diagnosing the localization of diseased tissue selected from the group consisting of an infarction and a necrosis comprising:

administering a compound selected from the group consisting of a porphyrin-complex and an expanded porphyrin-complex, said compound being specific for the localization;

allowing said compound to specifically accumulate in the localization; and detecting said compound in the localization.

2. The method of claim 1 wherein the localization resides in at least one organ selected from the group consisting of heart, kidney, intestine, lung and brain.

3. The method of claim 1 wherein the porphyrin-complex compound comprises a labeled metal selected from the group consisting of a radioactive metal, a paramagnetic metal and a super paramagnetic metal.

4. The method of claim 1 wherein the porphyrin-complex is administered in the amount of 0.001–1.0 mmol/kg body weight.

5. The method of claim 1 wherein the porphyrin-complex is gadolinium mesoporphyrin or manganese tetraphenylporphyrin.

* * * * *